United States Patent
Koh

(10) Patent No.: US 12,350,466 B2
(45) Date of Patent: Jul. 8, 2025

(54) APPARATUS FOR PATIENT-CONTROLLED DRUG INJECTION HAVING COUNTER

(71) Applicant: THE CATHOLIC UNIVERSITY OF KOREA INDUSTRY-ACADEMIC COOPERATION FOUNDATION, Seoul (KR)

(72) Inventor: Hyunjung Koh, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 848 days.

(21) Appl. No.: 17/627,228

(22) PCT Filed: Jul. 3, 2020

(86) PCT No.: PCT/KR2020/008752
§ 371 (c)(1),
(2) Date: Jan. 14, 2022

(87) PCT Pub. No.: WO2021/015444
PCT Pub. Date: Jan. 28, 2021

(65) Prior Publication Data
US 2022/0265917 A1    Aug. 25, 2022

(30) Foreign Application Priority Data
Jul. 19, 2019   (KR) .................. 10-2019-0087628

(51) Int. Cl.
*A61M 5/142*   (2006.01)
*A61M 5/145*   (2006.01)
(Continued)

(52) U.S. Cl.
CPC ........ *A61M 5/1428* (2013.01); *A61M 5/1454* (2013.01); *A61M 5/3158* (2013.01);
(Continued)

(58) Field of Classification Search
CPC .............. A61M 5/1428; A61M 5/1454; A61M 5/3158; A61M 2005/1405;
(Continued)

(56) References Cited

FOREIGN PATENT DOCUMENTS

| EP | 0941741 A2 * | 9/1999 |
|----|------|------|
| JP | 05015590 | 1/1993 |

(Continued)

OTHER PUBLICATIONS

International Search Report and Written Opinion issued in Corresponding PCT Application No. PCT/KR2020/008752, dated Dec. 18, 2020 (English Translation provided).

*Primary Examiner* — Bhisma Mehta
*Assistant Examiner* — Nelson Louis Alvarado, Jr.
(74) *Attorney, Agent, or Firm* — NORTON ROSE FULBRIGHT US LLP

(57) ABSTRACT

The present invention relates to an apparatus for patient-controlled drug injection having a counter capable of counting the number of administrations. According to one aspect of the present invention, disclosed is an apparatus for patient-controlled drug injection having a counter, comprising: a case; a pressing part, provided in the case, for applying pressure to pump a chemical liquid; and a counter, provided in the case and having a counting button that is pressed by pressure when a user presses the pressing part, for counting the number of times that the pressing part is pressed.

9 Claims, 6 Drawing Sheets

(51) Int. Cl.
*A61M 5/315* (2006.01)
*A61M 5/14* (2006.01)
*A61M 5/20* (2006.01)
*A61M 5/31* (2006.01)

(52) U.S. Cl.
CPC .............. *A61M 2005/1405* (2013.01); *A61M 2005/2086* (2013.01); *A61M 2005/3128* (2013.01); *A61M 2005/3154* (2013.01)

(58) Field of Classification Search
CPC .. A61M 2005/2086; A61M 2005/3128; A61M 2005/3154; A61M 5/1424; A61M 5/16809; A61M 2205/276; A61M 5/168; A61M 5/16881; A61M 5/16886; A61M 2205/3334
See application file for complete search history.

(56) References Cited

FOREIGN PATENT DOCUMENTS

| | | |
|---|---|---|
| JP | H11244394 | 9/1999 |
| JP | 2002058739 | 2/2002 |
| JP | 2004500223 | 1/2004 |
| JP | 2011224182 | 11/2011 |
| JP | 5569792 B2 * | 8/2014 |
| JP | 2015511528 | 4/2015 |
| JP | 2015511528 A * | 9/2015 |
| KR | 200449168 | 6/2010 |
| KR | 20190034923 | 4/2019 |

\* cited by examiner

APPARATUS FOR PATIENT-CONTROLLED DRUG INJECTION HAVING COUNTER

FIELD OF THE DISCLOSURE

The present invention relates to an apparatus for patient-controlled drug injection having a counter, which is capable of counting the number of administrations and guaranteeing an administration interval.

DESCRIPTION OF RELATED ART

In general, in the case of disease or injury, medical treatment through drug administration and the like is concurrently performed for the treatment, as well as surgical treatment such as surgery and the like, and in this case, regular drug administration is required.

In addition to oral administration through pills or the like, the administration of such drugs includes various methods such as administration through injection, application to the skin and the like.

Meanwhile, in the case of severe pain from surgery, cancer or the like, it is necessary to manage the pain through regular administration of drugs. Since these analgesics are often administered by injection, a medical professional is absolutely necessary for injection.

Therefore, since it is necessary to administer by injection by a medical professional for a certain period of time or whenever pain is felt, it may lead to waste of medical personnel.

In addition, since the patient has to wait for the medical personnel to arrive whenever he/she feels pain, the time when the patient feels pain becomes longer, if the patient waits for the medical personnel to arrive for a long period of time, which may cause discomfort and pain.

In order to solve this problem, patient-controlled analgesia (PCA) is used.

The patient-controlled analgesia is a device that allows a patient to self-administer drugs such as analgesics and the like, when the patient feels pain, and a manual type that injects a drug into a pre-secured infusion line with the user's pressing pressure, or an electric patient-controlled analgesia that injects a drug with power from a motor or the like is used.

However, analgesics used for patients with severe pain or injuries such as cancer and the like are often used with narcotic analgesics that cause hallucinations or addiction, and thus, the dosage and interval of administration must be checked. There is a problem in that the number of administrations is not counted, and there is a problem in that it is necessary to rely on the patient's memory or records, because the administration interval cannot be checked.

SUMMARY OF THE INVENTION

The present invention is to solve the above problems, and it is an object of the present invention to provide an apparatus for patient-controlled drug injection having a counter, which is capable of counting the number of administrations and preventing overuse or abuse.

In addition, it is another object of the present invention to provide an apparatus for patient-controlled drug injection having a counter, which is capable of keeping a minimum administration interval.

The problems of the present invention are not limited to the problems mentioned above, and other problems that are not mentioned will be clearly understood by those skilled in the art from the following description.

In order to solve the above problems, according to an exemplary embodiment of the present invention, disclosed is an apparatus for patient-controlled drug injection having a counter, including a case, a pressing part, provided in the case, for applying pressure to pump a chemical liquid, and a counter, provided in the case and having a counting button that is pressed by pressure when a user presses the pressing part, for counting the number of times that the pressing part is pressed.

The pressing part may include a cylinder body including a chemical liquid inlet through which a chemical liquid is introduced and a chemical liquid outlet through which a chemical liquid is discharged, and forming a chamber in which the introduced chemical liquid is temporarily stored, a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet, and an arm extending from the piston button and provided to press the counting button of the counter when the piston button is pressed.

The chemical liquid inlet and the chemical liquid outlet may be provided with a one-way valve for allowing the chemical liquid to flow only in one direction and preventing the chemical liquid from flowing in the reverse direction.

The pressing part may include a cylinder body which includes a chemical liquid inlet through which a chemical liquid is introduced and a chemical liquid outlet through which a chemical liquid is discharged, and may form a chamber in which the introduced chemical liquid is temporarily stored;

It may include a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet, and a plunger provided to press the counting button of the counter while being pushed and protruded by pressure of the chemical liquid flowing in one direction by the piston button.

The plunger may include a plunger housing formed with an inlet through which the chemical liquid discharged through the chemical liquid outlet is introduced, a plunger needle having one side provided inside the plunger housing and the other side slidably provided in the plunger housing so as to protrude to the outside of the plunger housing, and slidingly moved by pressure of the chemical liquid applied inside the plunger housing, and an outlet in communication with the plunger housing when the plunger needle is slid to one side by pressure of the chemical liquid to discharge the chemical liquid from the plunger housing.

A part provided inside the plunger housing of the plunger needle may include a counter provided to be in close contact with the inner circumferential surface of the plunger housing.

It may further include a timer for preventing from being pressed again within a certain period of time after the pressing part is pressed.

The timer may further include a mainspring which is rotated and wound when the pressing part is pressed, a cam rotated by the elastic force of the mainspring, wherein a part of the outer circumferential surface forms an arc having a longer diameter than the rest, and a latch for constraining the pressing part while being pressed according to the rotation angle of the cam, or elastically restoring to release the constraining of the pressing part.

The pressing part may include a cylinder body including a chemical liquid inlet through which a chemical liquid is introduced and a chemical liquid outlet through which a chemical liquid is discharged, and forming a chamber in which the introduced chemical liquid is temporarily stored, and a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet, and the latch may include a latch head having one end connected to the outer circumferential surface of the cam and pressed toward the piston button by the cam according to a rotation angle of the cam, a latch body provided to be stretchable with the latch head, and having the other end extending toward the groove of the piston button, and the other side provided to receive pressure from the side of the latch head, a forward piston provided between the latch head and the latch body, and elastically transmitting a pressing force that the latch head is pressed toward the piston button by the cam toward the latch body so as to elastically press the latch body toward the groove of the piston button, and a reverse piston for elastically supporting the latch body toward the case so as to elastically press the latch body in a direction opposite to the forward piston.

The elastic force of the forward spring may be provided to be greater than the elastic force of the reverse spring.

The timer may further include a rack formed the moving direction of the pressing part on the side of the pressing part, and a pinion meshed with the rack and rotated when the pressing part is pressed to wind the mainspring.

According to the apparatus for patient-controlled drug injection having a counter of the present invention, there are the following effects.

First, since the patient can self-administer a drug whenever he/she feels the symptoms, there is no need to wait for the medical staff to arrive, and thus, the patient's pain can be alleviated and the burden on the medical staff can be reduced.

Second, since the number of times the patient administers drugs can be counted, there is an effect of preventing abuse and overuse of drugs.

Third, since the minimum interval at which the patient administers drugs can be adjusted, there is an effect of preventing the addiction, abuse and overuse of drugs.

The effects of the present invention are not limited to the effects mentioned above, and other effects that are not mentioned will be clearly understood by those skilled in the art from the description of the claims.

BRIEF DESCRIPTION OF THE DRAWINGS

The detailed description of the preferred exemplary embodiments of the present application described below, as well as the summary set forth above, may be better understood when read in connection with the accompanying drawings. In the drawings, preferred exemplary embodiments are shown for the purpose of illustrating the present invention. However, it should be understood that the present application is not limited to the precise arrangements and means illustrated herein.

FIG. 5 is a cross-sectional view illustrating a state in which the plunger is closed; and FIG. 6 is a cross-sectional view showing a state in which the plunger is open.

DETAILED DESCRIPTION OF THE INVENTION

Figure 1:
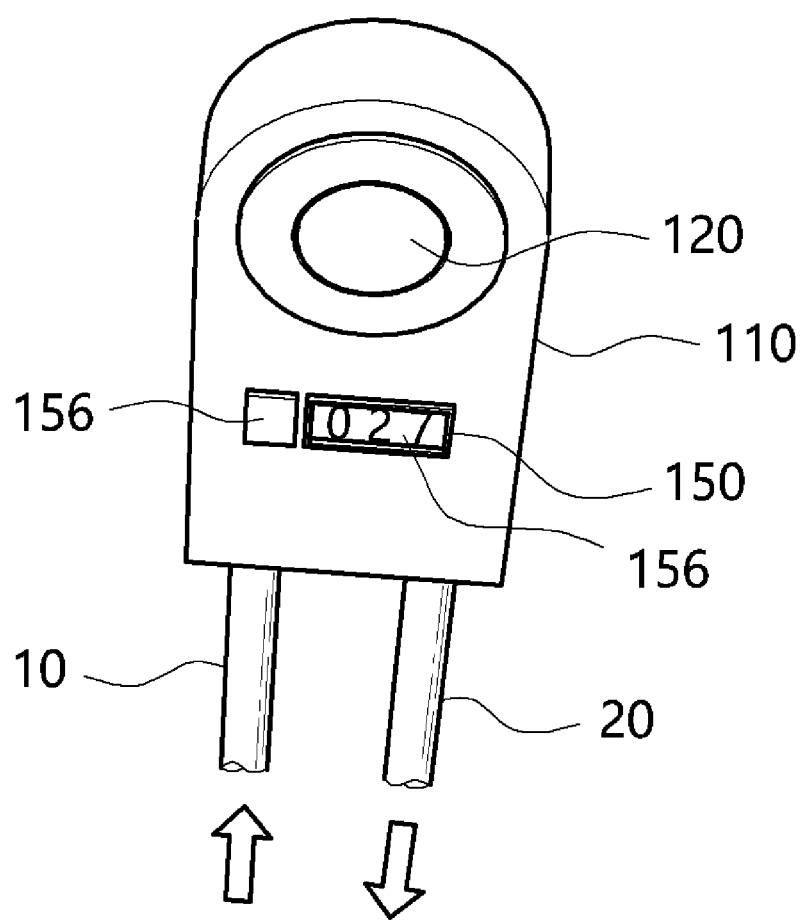
FIG. 1 is a perspective view illustrating an example of the apparatus for patient-controlled drug injection having a counter according to an exemplary embodiment of the present invention.

Hereinafter, preferred exemplary embodiments of the present invention in which the objects of the present invention can be realized in detail will be described with reference to the accompanying drawings. In the description of the present exemplary embodiments, the same name and the same reference numerals are used for the same configuration, and additional descriptions thereof will be omitted.

Hereinafter, an exemplary embodiment of the apparatus 100 for patient-controlled drug injection having a counter of the present invention will be described.

The apparatus for patient-controlled drug injection having a counter 100 according to the present exemplary embodiment may include a case 110, a pressing part 120 and a counter 150, as illustrated in FIG. 1.

The case 110 is a component forming an external shape and may be made of a material such as plastic, metal or the like. In addition, a supply pipe 10 through which a drug is supplied and a discharge pipe 20 through which the drug is discharged may be coupled to one side thereof.

Further, the case 110 may be provided with a pressing part 120 and a counter 150. The pressing part 120 is provided in the case 110 such that the user may press it with a hand or the like, and may be provided to be exposed to one side of the case 110.

In addition, the counter 150 is provided in the case 110, and it is a component that counts the number of times that the pressing part 120 is pressed by being provided with a counting button 154 which is pressed with the pressure when the user presses the pressing part 120 and a number display unit 152 that displays the current counted number. The number display unit 152 of the counter 150 may be covered with a transparent window such that the counter 150 may also check the number from the outside of the case 110.

The counter 150 is widely known, and may be formed in a mechanical or electronic manner, and for the detailed structure of such a counter 150, the description thereof will be omitted.

In addition, a reset button 156 which is capable of initializing the cumulative number of the counter 150 may be provided to be exposed to the outside of the case 110. In this case, in order to prevent the reset button 156 from being pressed unintentionally, an area corresponding to the reset button 156 of the case 110 may be opened, and the reset button 156 may be provided to be located on the lower side of the opened portion.

Figure 2:
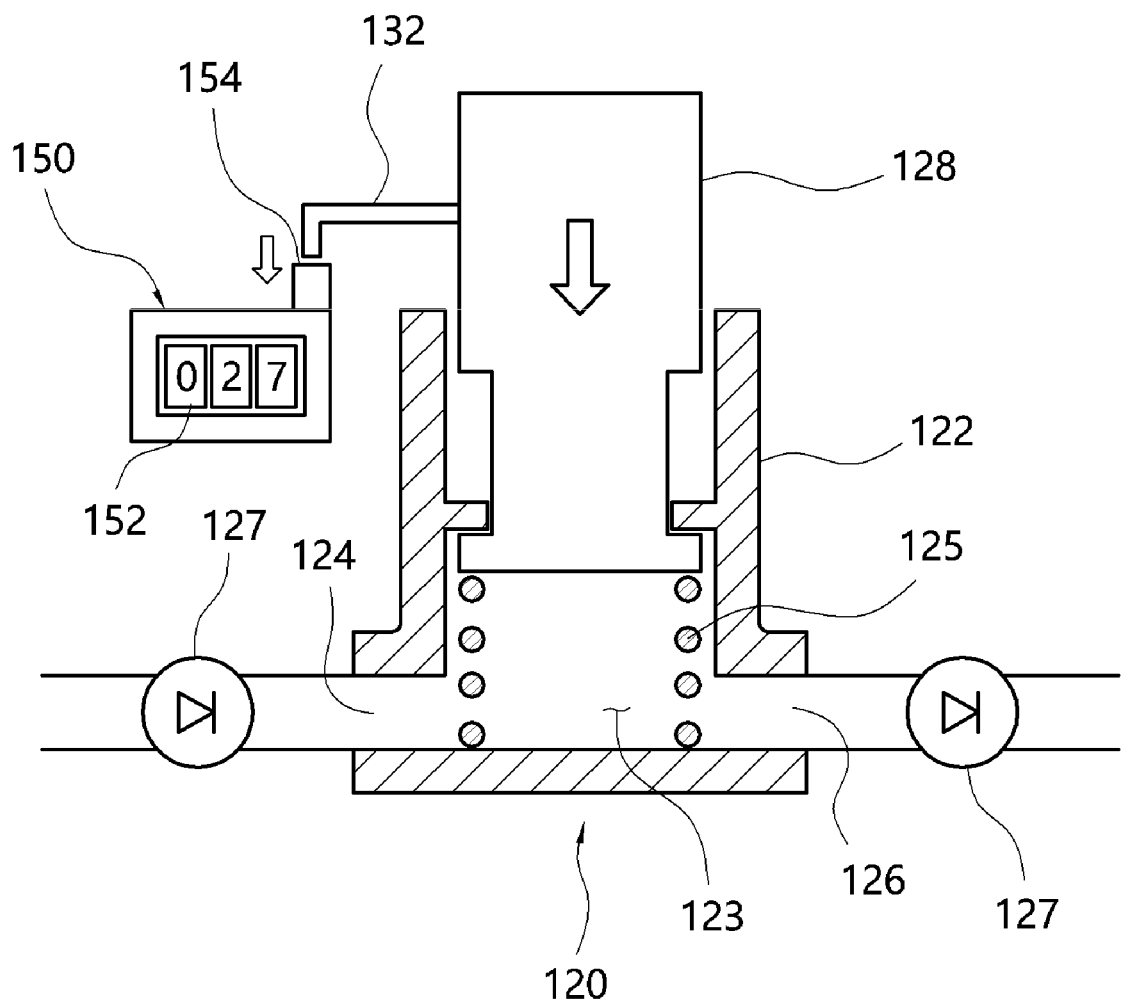
FIG. 2 is a cross-sectional view illustrating an exemplary embodiment of the pressing part of FIG. 1.

Meanwhile, the pressing part 120 may include a cylinder body 122, a piston button 128, an arm 132, a spring 125 and a one-way valve 127, as illustrated in FIG. 2.

The cylinder body 122 may be formed with a chemical liquid inlet 124 through which a chemical liquid is introduced and a chemical liquid outlet 126 through which a chemical liquid is discharged, and may form a chamber 123 in which the chemical liquid introduced from the chemical liquid inlet 124 is temporarily stored.

Herein, the chemical liquid may refer to, for example, an analgesic, but is not limited thereto.

The chemical liquid inlet 124 extends to the outside of the case 110 and may be connected to a tube connected to a bag in which the chemical liquid is stored, and the tube may be connected to the supply pipe 10.

In addition, the chemical liquid outlet 126 extends to the outside of the case 110 and may be connected through a tube connected to a catheter (not illustrated) inserted into a patient and a discharge pipe 20.

That is, the chemical liquid may be introduced from the bag, and may be supplied to the patient through the chamber 123 of the cylinder body 122.

In addition, the piston button 128 may be elastically supported so as to protrude from the cylinder body 122 to receive a user's pressing action. In addition, it may be provided to push the chemical liquid in the chamber 123 toward the chemical liquid outlet 126 while being introduced into the chamber 123 by the user's pressing action.

A spring 125 supporting the piston button 128 may be provided inside the chamber 123 to elastically support the piston button 128.

Meanwhile, the outer circumference of the piston button 128 in contact with the inner circumferential surface of the chamber 123 may be in close contact with the inner circumferential surface of the chamber 123.

In addition, the arm 132 may extend from the piston button 128 toward the counting button 154 of the counter 150, and may be provided to press the counting button 154 of the counter 150, when the piston button 128 is pressed.

In addition, the chemical liquid inlet 124 and the chemical liquid outlet 126 may be provided with a one-way valve 127 such as a valve or the like such that the chemical liquid flows in only one direction.

Therefore, when the user presses the piston button 128, the piston button 128 is lowered, pushing and thereby pumping the chemical liquid in the chamber 123 toward the chemical liquid outlet 126.

In this case, the arm 132 may also be counted by pressing the counting button 154 of the counter 150 while descending along the piston button 128 together.

Afterwards, the piston button 128 is raised by the elastic force of the spring 125, and a negative pressure is formed in the chamber 123, and the chemical liquid may be introduced into the chamber 123 through the chemical liquid inlet 124.

Meanwhile, after the pressing part 120 is pressed, a timer 160 may be further provided to prevent being pressed again within a certain period of time.

Figure 3:
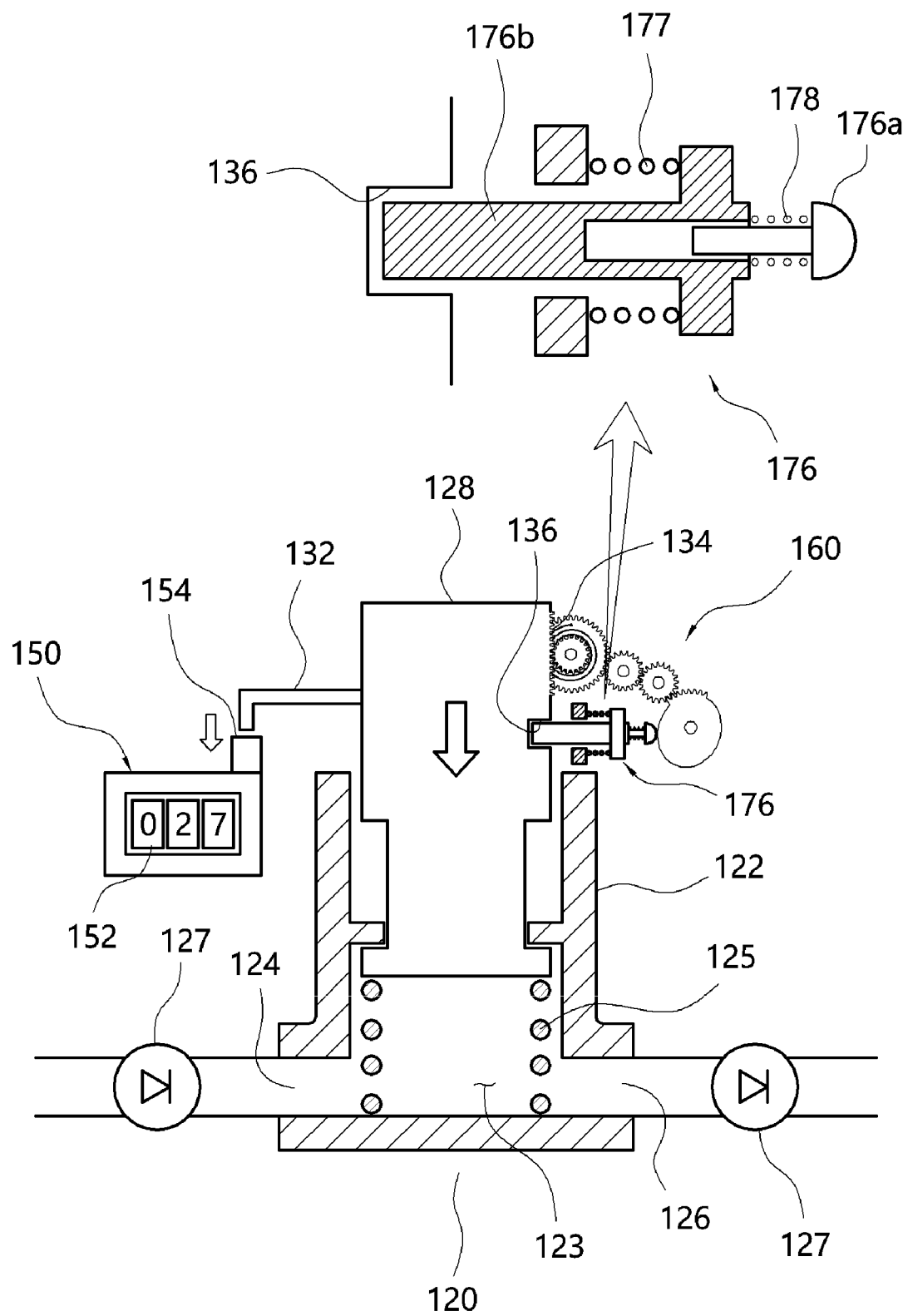
FIG. 3 is a cross-sectional view illustrating an example in which a timer is provided in the pressing part of FIG. 2.
Figure 4:
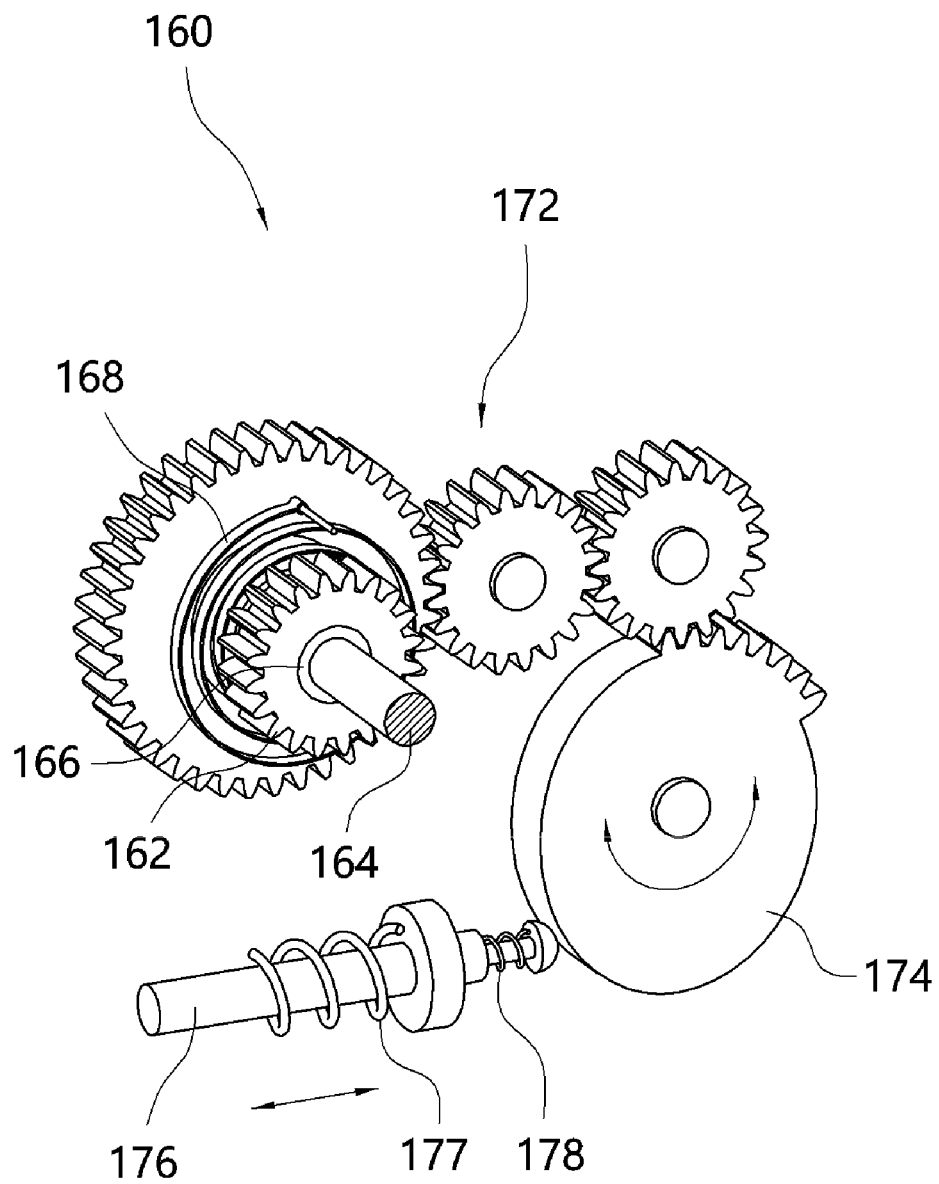
FIG. 4 is a perspective view illustrating an example of the timer of FIG. 3.

FIGS. 3 and 4 are views illustrating a structure in which a timer 160 is further provided in the structure of the pressing part 120 of FIG. 2.

As illustrated in FIGS. 3 and 4, the timer 160 may include a rack 134, a pinion 162, a rotating shaft 164, a one-way bearing 166, a mainspring 168, a gear part 172 and a latch 176.

The rack 134 may have a longitudinal direction in a direction in which the piston button 128 is pressed on a side surface of the piston button 128, and may be formed to have a plurality of teeth.

The pinion 162 may be meshed with the rack 134 and rotate together when the piston button 128 is pressed.

The rotating shaft 164 may be formed to pass through the rotation center of the pinion 162 and may be provided to form an axis of the rotation center of the pinion 162.

In addition, the one-way bearing 166 may be disposed between the pinion 162 and the rotating shaft 164, and it is a component that transmits the rotational force of the pinion 162 in only one direction, and does not transmit the rotational force by idling when rotating in the opposite direction.

The mainspring 168 is axially coupled to the rotating shaft 164 and is wound by the rotation of the rotating shaft 164 according to the rotation of the pinion 162 when the piston button 128 is pressed, and it may be gradually rotated for a certain period of time in the opposite direction by the elastic force when the rotational force of the pinion 162 is not applied.

Meanwhile, the cam 174 is rotated by the rotational force of the mainspring 168, and some of the outer circumferential surfaces may be formed to form an arc having a longer diameter than the rest.

In addition, a gear unit 172 made of one or more gears is provided between the mainspring 168 and the cam 174 so as to transmit the rotational force of the mainspring 168 to the cam 174. The rotation angle of the cam 174 to be described below may be determined as a rotation ratio of gears constituting the gear unit 172.

In addition, the rear end of the latch 176 may be supported by the cam 174 and may be elastically supported by a reverse spring 177 or the like at an arbitrary location inside the case 110.

In addition, a groove 136 into which the latch 176 may be inserted may be formed on a side of the piston button 128. In addition, the rear end of the latch 176 supported by the cam 174 may be provided to be elastically stretched by a forward spring 178 or the like.

When described in more detail, the latch 176 may include a latch body 176*b* and a latch head 176*a*, as illustrated in FIG. 3.

The latch head 176*a* may have one end supported on the outer circumferential surface of the cam 174, and may be provided to be pressed toward the piston button 128 by the cam 174 according to the rotation angle of the cam 174.

The latch head 176*a* may be provided to be stretchable with respect to the latch body 176*b*. In addition, a forward spring 178 may be provided between the latch head 176*a* and the latch body 176*b* so as to apply an elastic force to each other between the latch head 176*a* and the latch body 176*b*.

Meanwhile, the latch body 176*b* may have one end extending toward the groove 136, and may be provided such that an elastic force is applied in both directions by the forward spring 178 and the reverse spring 177.

The latch head 176*a* may be provided to be slidable with respect to the latch body 176*b* such that the latch 176 may be stretched, and the forward spring 178 may be provided between the latch head 176*a* and the latch body 176*b* so as to be provided to elastically transmit the applied pressing force toward the latch body 176*b* when the latch head 176*a* is pressed toward the piston button 128 by the cam 174.

Therefore, when the piston button 128 is pressed, the pinion 162 is also rotated, and the mainspring 168 may be wound accordingly. As the pinion 162 is rotated, the rotating shaft 164 is also rotated, and accordingly, the plurality of gear units 172 transmits the rotational force to the cam 174 such that the cam 174 may rotate.

As the cam 174 is rotated, the latch 176 may advance toward the piston button 128, and in this case, while the piston button 128 is in a lowered state, since the positions of the groove 136 formed on the side of the piston button 128 and the latch 176 do not match with each other, the forward spring 178 formed at the rear end of the latch 176 and the latch 176 may be compressed to store the elastic force.

Meanwhile, when the piston button 128 is elevated and the groove 136 formed on the side surface of the piston button 128 and the position of the latch 176 coincide, the front end of the latch 176 may be inserted into the groove 136 by the elastic force of the forward spring 178 provided at the rear end of the latch 176.

In addition, the cam 174 rotates for a certain period of time according to the rotational force of the mainspring 168, and while the latch 176 is supported by the cam 174, it is not removed from the groove 136, and thus, the piston button 128 is not pressed.

In addition, when the cam 174 is rotated by a certain angle or more and the latch 176 is not supported by the cam 174, as the latch 176 moves backward by the elastic force of the reverse spring 177, the latch 176 is removed from the groove 136, and from this point on, the piston button 128 may be pressed.

In this case, the elastic force of the forward spring 178 may be formed to be greater than the elastic force of the reverse spring 177.

That is, while the latch 176 is supported by the cam 174, the piston button 128 is prevented from being pressed, thereby guaranteeing an administration interval.

Hereinafter, another exemplary embodiment of the pressing part 220 will be described.

Figure 5:
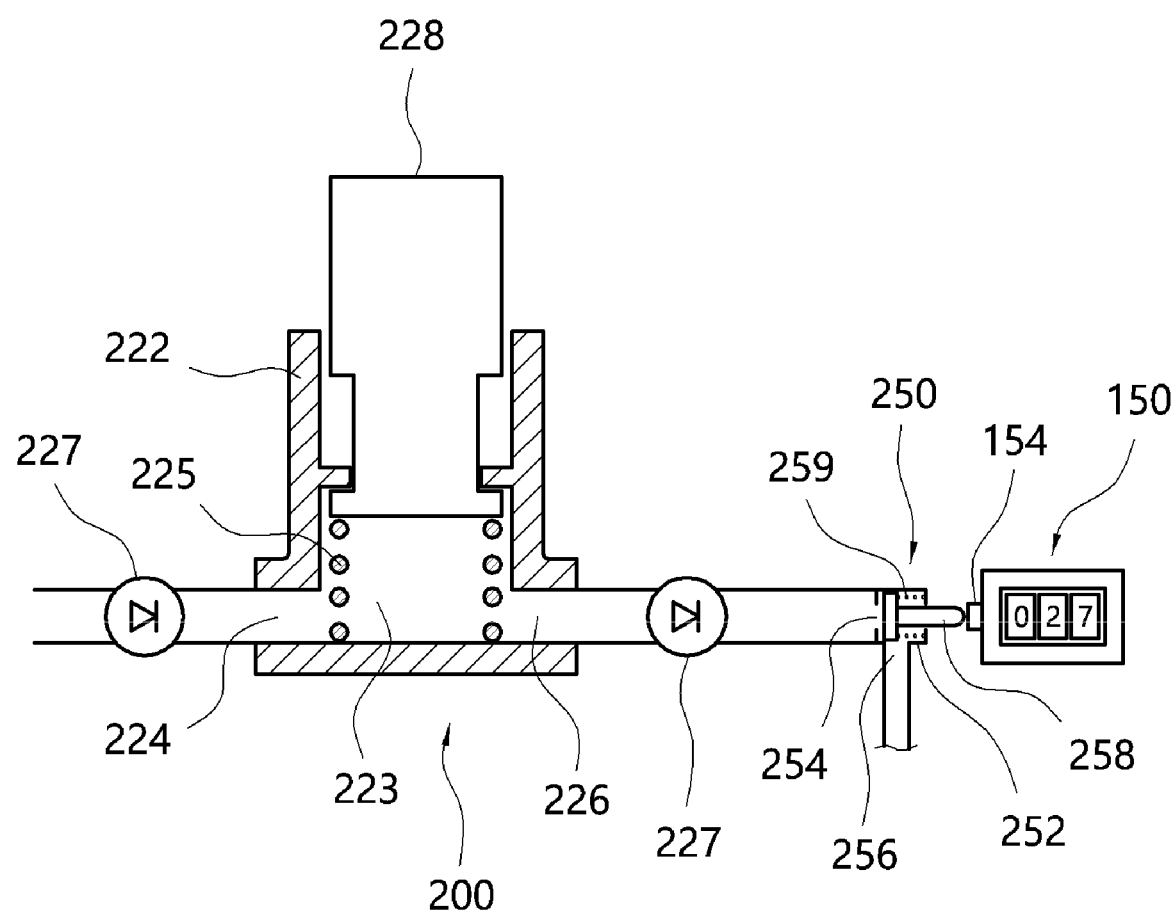
FIGS. 5 and 6 are cross-sectional views illustrating another exemplary embodiment of the pressing part of FIG. 1.
Figure 6:
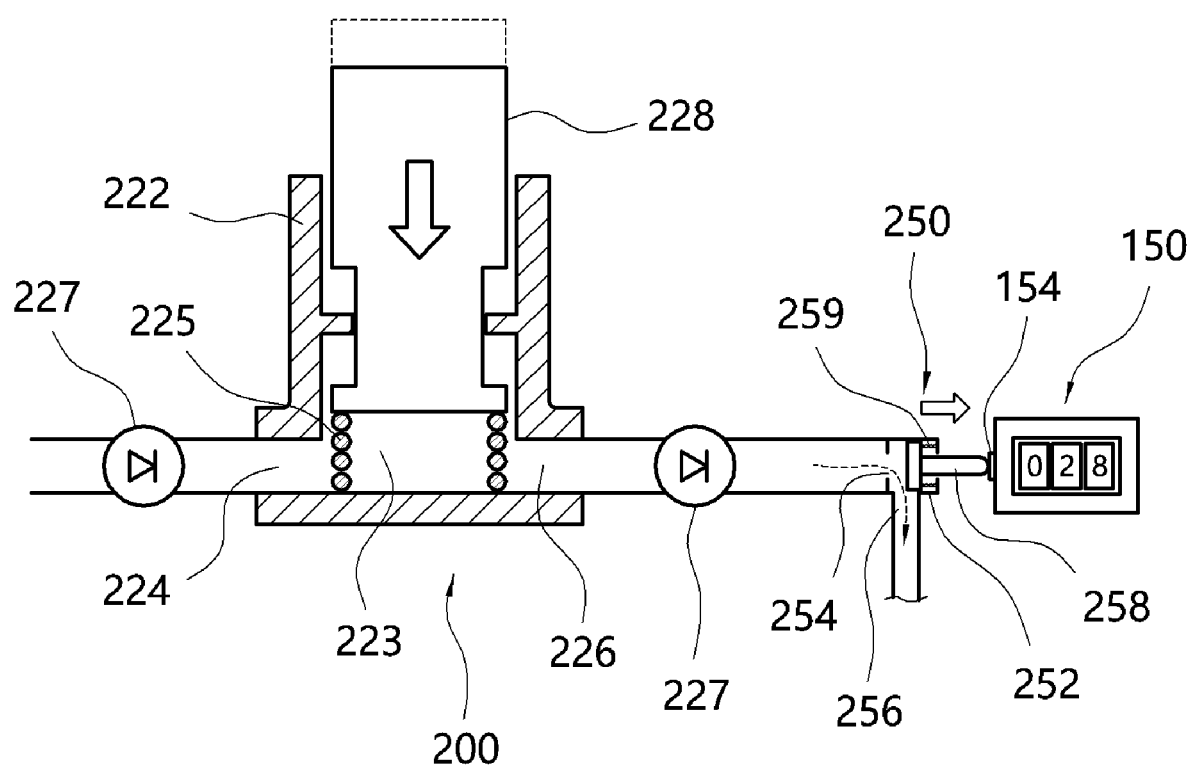

The pressing part 220 according to the present exemplary embodiment may include a cylinder body 222, a piston button 228 and a plunger 250, as illustrated in FIGS. 5 and 6.

Since the cylinder body 222 and the piston button 228 are substantially identical to the cylinder body 122 and the piston button 128 of the above-described exemplary embodiment, the detailed descriptions thereof will be omitted.

The plunger 250 may include a plunger housing 252, a plunger needle 258 and an outlet 256.

The plunger housing 252 may form the external shape of the plunger 250.

The plunger housing 252 may form an inlet 254 through which the chemical liquid discharged through the chemical liquid outlet 226 flows into, and an outlet 256 through which the chemical liquid inside the plunger housing 252 is discharged.

In addition, the plunger needle 258 is provided inside the plunger housing 252 and may be elastically supported by a spring 259.

In addition, the plunger needle 258 may have one side provided inside the plunger housing 252 and the other side formed to protrude to the outside of the plunger housing 252, and may be provided to slide by being pushed by the pressure of the chemical liquid applied to the plunger housing 252.

That is, a hole through which the other end of the plunger needle 258 passes may be formed in the plunger housing 252, and the other end of the plunger needle 258 may pass through the hole and protrude outward to be extended to the vicinity of the counting button 154 of the counter 150.

In addition, a part of the plunger needle 258 located inside the plunger housing 252 may be provided in close contact with the inner circumferential surface of the plunger needle 258 so as to completely receive the pressure of the chemical liquid.

In addition, the outlet 256 may communicate with the plunger housing 252 when the plunger needle 258 is slid to one side by the pressure of the chemical liquid, and may be formed at a position blocked from the plunger housing 252, when the plunger needle 258 is restored to its initial position by the elastic force of the spring 259.

Accordingly, as illustrated in FIG. 6, when the piston button 228 is pressed, the chemical liquid inside the chamber 223 may be introduced into the plunger housing 252 through the chemical liquid outlet 226 and the inlet 254. In this case, as the plunger needle 258 is pushed and moved by the pressure of the chemical liquid, the other end of the plunger needle 258 may be counted by pressing the counting button 154 of the counter 150.

Meanwhile, as the plunger needle 258 is moved to one side, the outlet 256 may communicate with the plunger housing 252, and the chemical liquid may be discharged through the outlet 256 and administered to the body.

As described above, preferred exemplary embodiments according to the present invention have been reviewed, and the fact that the present invention can be embodied in other specific forms without departing from the spirit or scope thereof, other than the above-described exemplary embodiments, is apparent to those skilled in the art. Therefore, the above-described exemplary embodiments should be regarded as illustrative rather than restrictive, and accordingly, the present invention is not limited to the above description and may be modified within the scope of the appended claims and equivalents thereof.

The invention claimed is:

1. An apparatus for patient-controlled drug injection having a counter, comprising:
    a case;
    a pressing part, provided in the case, for applying pressure to pump a chemical liquid; and
    a counter, provided in the case and having a counting button that is pressed by pressure when a user presses the pressing part, for counting the number of times that the pressing part is pressed,
    wherein the counter includes a timer for preventing the pressing part from being pressed again within a certain period of time after the pressing part is pressed, and
    wherein the timer comprises:
        a mainspring which is rotated and wound when the pressing part is pressed;
        a cam rotated by the elastic force of the mainspring, wherein a part of an outer circumferential surface of the cam forms an arc having a longer diameter than the rest; and
        a latch for constraining the pressing part while being pressed according to the rotation angle of the cam, or elastically restoring to release the constraining of the pressing part.

2. The apparatus of claim 1, wherein the pressing part comprises:
    a cylinder body comprising a chemical liquid inlet through which the chemical liquid is introduced and a chemical liquid outlet through which the chemical liquid is discharged, and forming a chamber in which the introduced chemical liquid is temporarily stored;
    a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet; and
    an arm extending from the piston button and provided to press the counting button of the counter when the piston button is pressed.

3. The apparatus of claim 2, wherein the chemical liquid inlet and the chemical liquid outlet are provided with a one-way valve for allowing the chemical liquid to flow only in one direction and preventing the chemical liquid from flowing in the reverse direction.

4. The apparatus of claim 1, wherein the pressing part comprises:
- a cylinder body comprising a chemical liquid inlet through which the chemical liquid is introduced and a chemical liquid outlet through which the chemical liquid is discharged, and forming a chamber in which the introduced chemical liquid is temporarily stored;
- a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet; and
- a plunger provided to press the counting button of the counter while being pushed and protruded by pressure of the chemical liquid flowing in one direction by the piston button.

5. The apparatus of claim 4, wherein the plunger comprises:
- a plunger housing formed with an inlet through which the chemical liquid discharged through the chemical liquid outlet is introduced;
- a plunger needle having one side provided inside the plunger housing and the other side slidably provided in the plunger housing so as to protrude to the outside of the plunger housing, and slidingly moved by pressure of the chemical liquid applied inside the plunger housing; and
- an outlet in communication with the plunger housing when the plunger needle is slid to one side by pressure of the chemical liquid to discharge the chemical liquid from the plunger housing.

6. The apparatus of claim 5, wherein a part provided inside the plunger housing of the plunger needle includes the counter provided to be in close contact with the inner circumferential surface of the plunger housing.

7. The apparatus of claim 1, wherein the pressing part comprises a cylinder body comprising a chemical liquid inlet through which the chemical liquid is introduced and a chemical liquid outlet through which the chemical liquid is discharged, and forming a chamber in which the introduced chemical liquid is temporarily stored, and a piston button which is elastically supported in a direction protruding from the cylinder body so as to receive a user's pressing action, is drawn into the chamber of the cylinder body by the user's pressing action, and pushes the chemical liquid in the chamber toward the chemical liquid outlet, and wherein the latch comprises:
- a latch head having one end connected to the outer circumferential surface of the cam and pressed toward the piston button by the cam according to a rotation angle of the cam;
- a latch body provided to be stretchable with the latch head, and having the other end extending toward a groove of the piston button, and the other side provided to receive pressure from a side of the latch head;
- a forward piston provided between the latch head and the latch body, and elastically transmitting a pressing force that the latch head is pressed toward the piston button by the cam toward the latch body so as to elastically press the latch body toward the groove of the piston button; and
- a reverse piston for elastically supporting the latch body toward the case so as to elastically press the latch body in a direction opposite to the forward piston.

8. The apparatus of claim 7, wherein the elastic force of the forward spring is provided to be greater than the elastic force of the reverse spring.

9. The apparatus of claim 1, wherein the timer further comprises:
- a rack formed along the moving direction of the pressing part on the side of the pressing part; and
- a pinion meshed with the rack and rotated when the pressing part is pressed to wind the mainspring.

* * * * *